US00PP31075P3

(12) United States Plant Patent
Neumüller

(10) Patent No.: US PP31,075 P3
(45) Date of Patent: Nov. 19, 2019

(54) APPLE TREE NAMED 'BAY 4210'

(50) Latin Name: ***Malus domestica* (Borkh.)**
Varietal Denomination: Bay 4210

(71) Applicant: Michael Neumüller, Hallbergmoos (DE)

(72) Inventor: Michael Neumüller, Hallbergmoos (DE)

(73) Assignee: Varieties International, LLC, Dundee, OR (US)

( * ) Notice: Subject to any disclaimer, the term of this patent is extended or adjusted under 35 U.S.C. 154(b) by 0 days.

(21) Appl. No.: 15/732,597

(22) Filed: Nov. 30, 2017

(65) Prior Publication Data

US 2018/0160580 P1 Jun. 7, 2018

Related U.S. Application Data

(60) Provisional application No. 62/497,759, filed on Dec. 1, 2016.

(51) Int. Cl.
*A01H 5/08* (2018.01)
*A01H 6/74* (2018.01)

(52) U.S. Cl.
USPC ..... Plt./172
CPC ..... *A01H 6/7418* (2018.05); *A01H 5/08* (2013.01)

(58) Field of Classification Search
USPC ..... Plt./172
CPC ..... A01H 5/08; A01H 6/7418
See application file for complete search history.

*Primary Examiner* — Keith O. Robinson
(74) *Attorney, Agent, or Firm* — The Webb Law Firm

(57) ABSTRACT

A new and distinct *Malus domestica* (Borkh.) variety that bears fruits having a yellow skin color and good eating and keeping qualities.

3 Drawing Sheets

Botanical classification: *Malus domestica* (Borkh.).
Varietal denomination: 'Bay 4210'.

BACKGROUND OF THE INVENTION

The present invention comprises a new and distinct variety of apple tree, botanically known as *Malus domestica* (Borkh.), and referred to by the varietal name 'Bay 4210'.

The new variety is the result of a planned breeding program conducted by the inventor in Hallbergmoos, Germany with the purpose of providing a new apple variety that exhibits tolerance to apple scab disease and good eating and keeping qualities. The new variety is the result of a cross between 'Pinova' (female parent, U.S. Plant Pat. No. 11,601) and 'Topaz' (male parent, unpatented). 'Bay 4210' was first asexually reproduced in Hallbergmoos, Germany by grafting in 2010.

The new variety is similar to 'Pinova' in its creamy yellow flesh color, but differs from 'Pinova' in skin color (yellow for 'Bay 4210' vs. red with yellow and pink for 'Pinova'). The new variety is similar to 'Topaz' in fruit shape and growth habit, but differs from 'Topaz' in aroma and skin color (yellow for 'Bay 4210' vs. red with yellow and pink for 'Topaz'). When compared to 'Golden Delicious' (unpatented), 'Bay 4210' exhibits a yellow skin color of RHS 12A, while 'Golden Delicious' exhibits a yellow-green skin color of RHS 145C. Further, when compared to other apple varieties known to the breeder, the new variety generally differs in its bright yellow skin color at picking maturity.

The new variety has been trial and field tested and has been found to retain its distinctive characteristics and remain true to type through successive asexual propagations.

DESCRIPTION OF THE DRAWINGS

The accompanying photographic drawings illustrate the new cultivar at approximately 5-6 years of age, with the color being as nearly true as possible with color illustrations of this type. It should be noted that colors may vary with growing conditions and time of year.

DESCRIPTION OF THE PLANT

Figure 1:
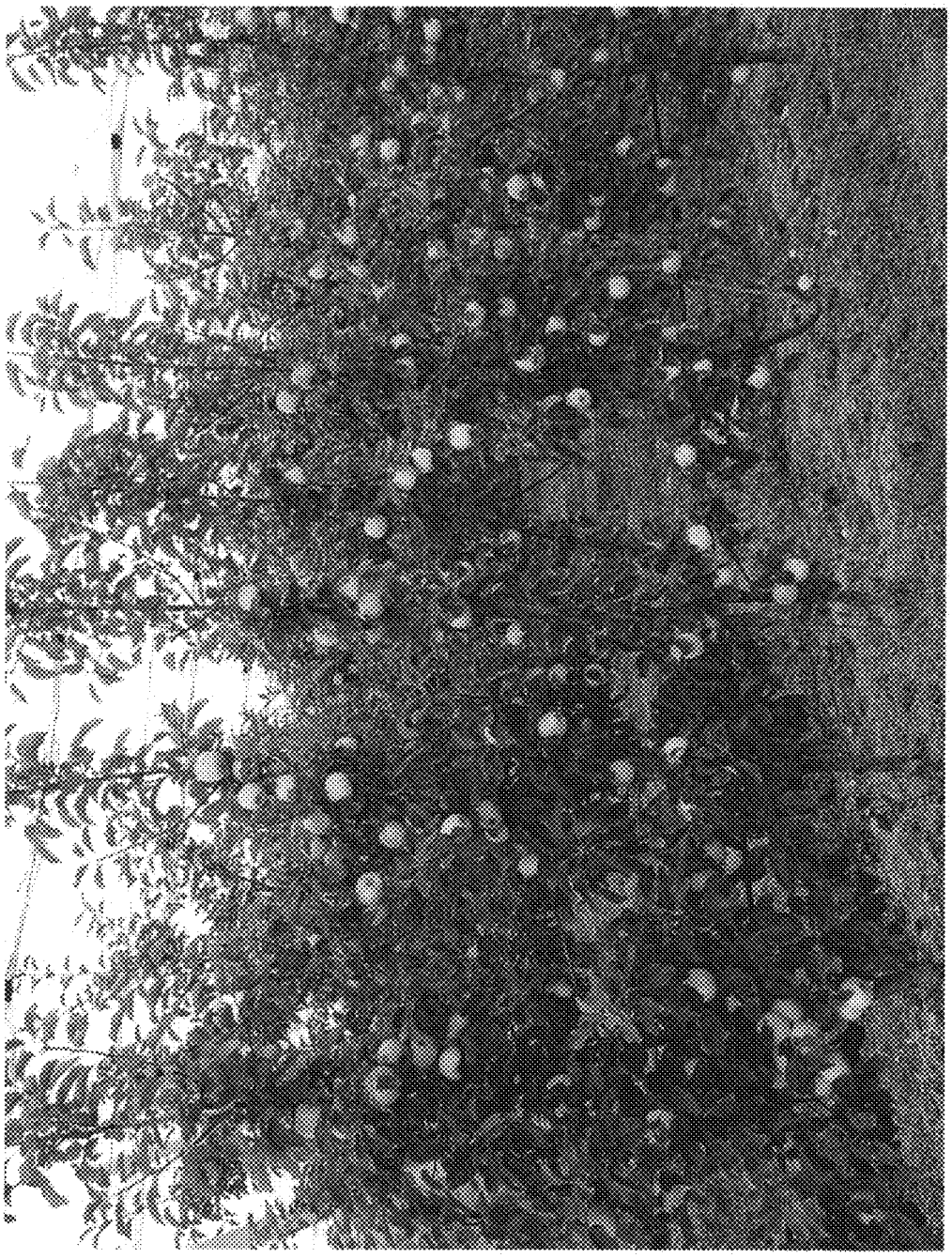
FIG. 1 illustrates multiple trees of the new variety.
Figure 2:
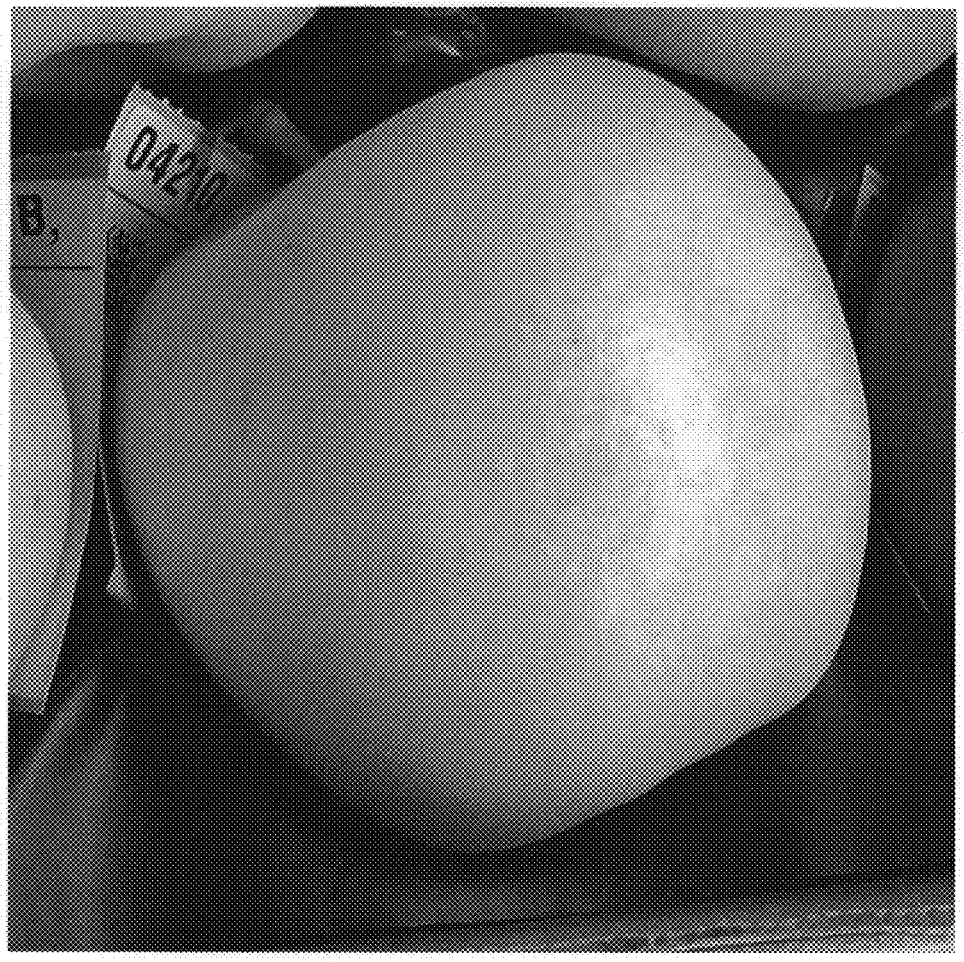
FIG. 2 illustrates a close-up view of the mature fruit of the new variety.
Figure 3:
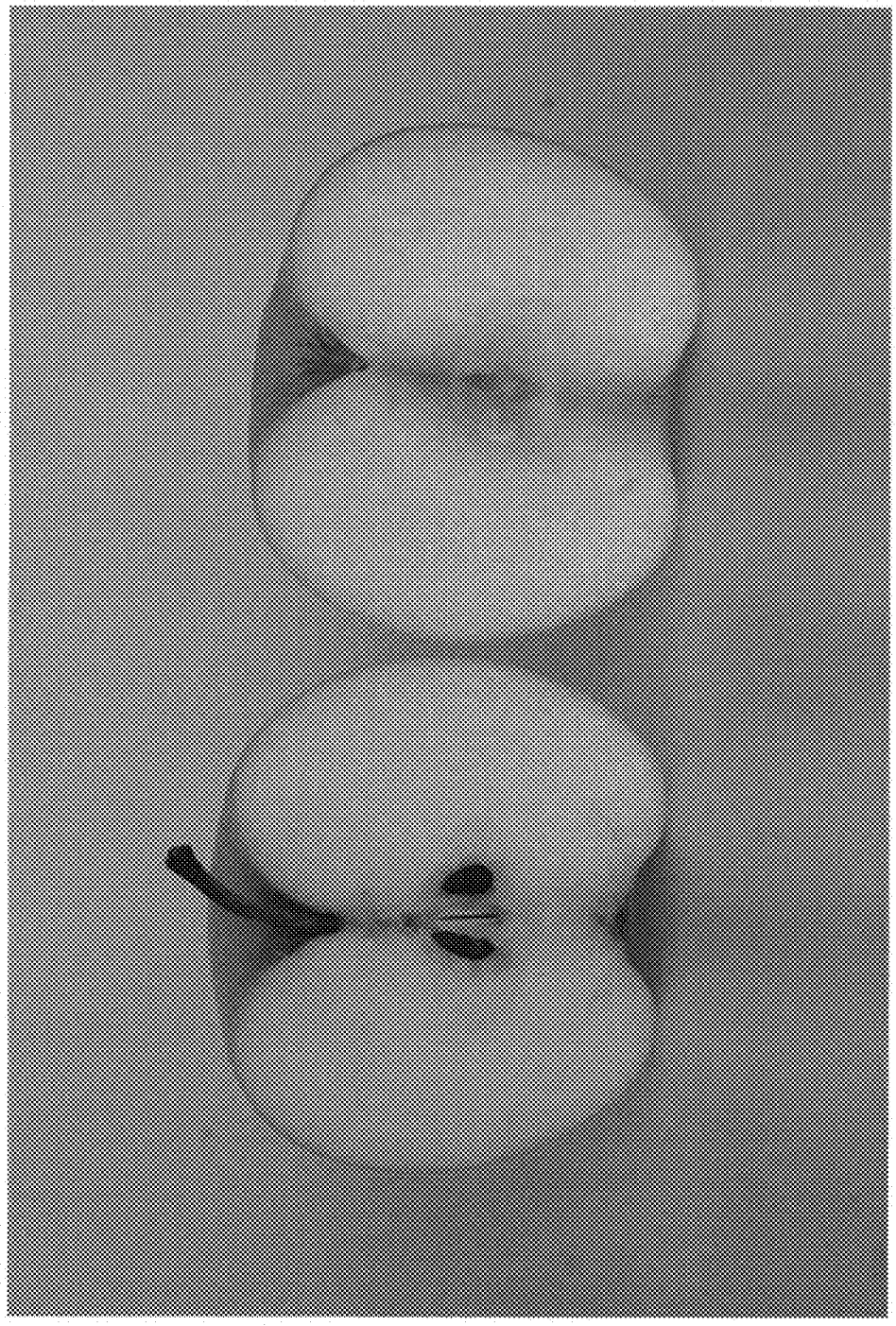
FIG. 3 illustrates a close-up view of the mature fruit of the new variety when cut in half.

The following detailed description sets forth characteristics of the new cultivar. The new variety was grown under natural field conditions in Hallbergmoos, Germany Color references are primarily to The 2005 R.H.S. Colour Chart of The Royal Horticultural Society of London, and were identified under natural light.

TREE

Age: Approximately 5-6 years.
Type: Ramified.
Size: Crown height of 2.5 m.
Vigor: Moderate.
Production: Highly productive.
Growth type: Upright and slightly spreading.
Bearing: Annual.
One-year old shoot:
*Internode length.*—15-20 mm.
*Average number of lenticels.*—11/cm of shoot length.
Leaf blade:
*Attitude in relation to shoot.*—Upwards.
*Length.*—70 mm.
*Width.*—40 mm.

*Color*.—RHS 137A.
*Shape*.—Oval.
*Upper surface texture*.—Medium glossy.
*Lower surface texture*.—Medium glossy with slight pubescence.
*Apex*.—Acute.
*Base*.—Ovate.
*Margin*.—Serrate.
*Venation*.—Pinnate main veins with netted secondary veins.
*Petiole length*.—23 mm.

Flower:
*Approximate date of beginning of flowering*.—Early-medium (Around April 20$^{th}$ in Hallbergmoos, Germany.
*Length*.—40-42 mm.
*Width*.—35-42 mm.
*Fragrance*.—Strong.
*Petals*.—Arrangement: Free. Number per flower: 5. Shape: Ovate. Apex: Rounded. Base: Caudate. Margin: Entire. Texture (both surfaces): Smooth and wavy. Color: Upper surface: RHS N155D and RHS 70C. Lower surface: RHS N155D and RHS N74C.
*Sepals*.—Number per flower: 5. Length: 9.2 mm. Width: 4.0 mm at sepal union. Shape: Triangular with an acute apex. Apex: Acute. Base: Wide and connected. Texture (both surfaces): Moderate pubescence present. Color: Upper surface: RHS N155D and RHS 70C. Lower surface: RHS N155D and RHS N74C.

Flower buds:
*Shape*.—Globose.
*Length*.—17.6 mm (without petiole) and 36 mm (with petiole).
*Width*.—15.5 mm.
*Color*.—RHS 63B and RHS N155B.

Fruit:
*Approximate date of time of eating maturity*.—From October to June in Hallbergmoos, Germany.
*Maturity when described*.—Full eating maturity.
*Skin color*.—RHS 12A.
*Skin bloom*.—Weak.
*Over color*.—Absent (on mature trees).
*Area of russet*.—Around stalk attachment to fruit: Small. Around the eye basin of fruit: Absent.
*Eye*.—Height: 10 mm. Diameter: 31 mm. Size: Medium. Basin depth: 5-8 mm. Basin width: 9-11 mm.
*Stalk*.—Length: 23-35 mm. Thickness: Medium. Cavity depth: 15-20 mm. Cavity width: 27-32 mm.
*Flesh*.—Aroma: Citrus-like. Color: RHS 4D. Firmness: Firm.
*Aperture of locules in transverse section*.—Slightly open.

Reproductive organs:
*Position of stigmas relative to flower anthers*.—Above.
*Stamen number*.—17.
*Filament*.—Length: 8 mm. Color: RHS N155B.
*Anther*.—Shape: Oval. Length: 1.8 mm. Color: RHS 8C.
*Pollen*.—Amount: Abundant. Color: RHS 6A.
*Stigma*.—Shape: Round. Color: RHS 145A.
*Ovary color*.—RHS 144A, with pubescence removed.

Seeds:
*Length*.—8.5-9.2 mm.
*Width*.—4.5-5.2 mm.
*Color*.—RHS 165A, immediately after extraction from core.
*Texture*.—Smooth, when fresh and not dried.

Keeping quality: High.
Tree winter hardiness: High.
Bud winter hardiness: High.
Disease resistance: Tolerant to apple scab (caused by *Venturia inaequalis*).

I claim:

1. A new and distinct variety of *Malus domestica* (Borkh.) apple tree plant substantially as is herein described and illustrated.

* * * * *